United States Patent
Rowell

(10) Patent No.: US 8,340,985 B2
(45) Date of Patent: *Dec. 25, 2012

(54) SYSTEM AND METHOD FOR SELLING INTANGIBLE PROPERTY

(75) Inventor: Michael Rowell, Issaquah, WA (US)

(73) Assignee: Efinancial, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/047,446

(22) Filed: Mar. 14, 2011

(65) Prior Publication Data

US 2011/0166870 A1    Jul. 7, 2011

Related U.S. Application Data

(63) Continuation of application No. 12/171,276, filed on Jul. 10, 2008, now Pat. No. 7,949,549, which is a continuation of application No. 10/936,455, filed on Sep. 7, 2004, now abandoned.

(60) Provisional application No. 60/500,440, filed on Sep. 4, 2003.

(51) Int. Cl.
*G06Q 40/00* (2006.01)

(52) U.S. Cl. .............. 705/4; 705/2; 705/3; 705/7; 707/9

(58) Field of Classification Search ............... 705/2–4, 705/7; 707/9; 386/52
See application file for complete search history.

(56) References Cited

U.S. PATENT DOCUMENTS

2002/0077998 A1 * 6/2002 Andrews et al. ................. 707/1

* cited by examiner

*Primary Examiner* — Michelle Le
(74) *Attorney, Agent, or Firm* — K&L Gates LLP

(57) ABSTRACT

A method comprises analyzing the psychology of a typical consumer and defining first key stages wherein customers drop out and second key stages wherein sales could be maximized.

11 Claims, 1 Drawing Sheet

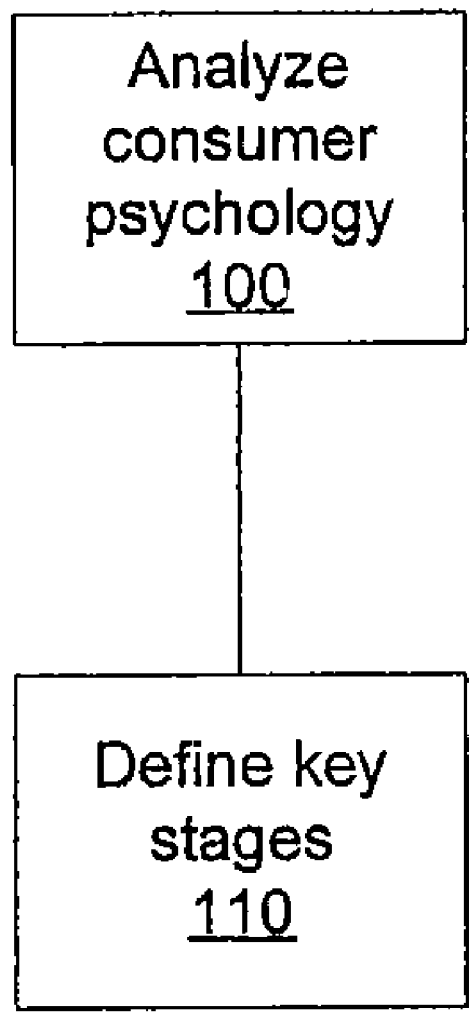

SYSTEM AND METHOD FOR SELLING INTANGIBLE PROPERTY

CROSS REFERENCE TO RELATED APPLICATION

The present application is a continuation of U.S. patent application Ser. No. 12/171,276, filed Jul. 10, 2008, now U.S. Pat. No. 7,949,549, which is a continuation of U.S. patent application Ser. No. 10/936,455, filed Sep. 7, 2004, now abandoned which is a non-provisional application of U.S. Provisional Patent Application No. 60/500,440, filed Sep. 4, 2003, the entire disclosures of each of which are incorporated herein by reference.

BACKGROUND OF THE INVENTION

Insurance agents spend the majority of their time tracking, following-up, and processing their sales and very little time actually selling.

SUMMARY OF THE INVENTION

The present system and method was developed specifically to increase the volume of insurance an agent could sell. It applies equally to any other intangible product such as mortgages, even though the explanation below focuses on insurance.

BRIEF DESCRIPTION OF THE DRAWINGS

FIG. 1 is a flow diagram of a method according to an embodiment of the invention.

DETAILED DESCRIPTION

Referring to FIG. 1, part of the development of this system and method includes analyzing 100 the psychology of the typical consumer and defining 110 key stages where customers drop out and other key stages where sales could be maximized. This system and method addresses the lengthy process required to buy life insurance by establishing what events must occur to move a customer through the process as quickly as possible with as little of effort by the selling agent.

The disclosed system and method is all inclusive for tracking and management of leads, including how leads are purchased, entered, distributed, emailed, monitored, and completely managed as they flow through the sales cycle.

All sales of intangible property such as life insurance follows the same general sales cycle from start to finish. A lead is imported or entered into the system. The prospective customer is then contacted, given a quote, and often agrees to purchase a policy. The customer must then complete an application that is specific to the state and company for which they are seeking insurance or other intangible product. The customer is also required to complete a medical exam.

Upon completing both the medical exam and application, the customer's information is sent off to the life insurance company where it will be reviewed by an underwriter. The underwriter uses predetermined underwriting guidelines to evaluate the customer's risk of death and place them into an appropriate rating classification. The rating classification determines the price for insurance the customer will be paying. Upon approval of the policy, the insurance company issues a policy and forwards it to the agent. The agent is then responsible for getting that policy to the customer and collecting any delivery requirements the insurance company has requested. The agent submits the delivery requirements to the insurance company and then follows up with the customer periodically.

Sales Cycle Breakdown:
New Lead—Gold, Silver, Bronze
New Applicant
Medical Complete
Paperwork Complete
Underwriting
Approved
Policy Sent
Client
Future Call Back
Dead File Sales Cycle Definitions:
New Lead
  Someone that has requested an agent to call them and give them a quote for insurance.
New Applicant
  Someone that has agreed to purchase a policy and you have mailed the application out to them and ordered the medical exam.
Medical Complete
  The customer has completed the medical exam but you are still waiting for their application.
Paperwork Complete
  Opposite of medical complete. They have completed the application but have not completed the medical exam.
Underwriting
  Person has completed both the medical and application and is being reviewed by an underwriter for the coverage they are requesting.
Approved
  Policy has been approved and the agent is awaiting the policy from the insurance company.
Policy Sent
  Policy was received and mailed out to the customer.
Client
  Policy was successfully delivered and all money and signatures to complete the transaction were completed.
Future Call Back
  Someone that is a prospect in the future for insurance. Usually you spoke to them and they asked you to contact them at a later date.
Dead File
  Someone you were either unable to contact or after contacting them you determined that they are not going to be a prospect for the insurance.

This system and method additionally includes several reporting features for agents and agencies to spot problem areas in their business. The system allows for users to run reports on their business to see average case sizes, number of people in each sales stage, and graphical analysis of a user's book of business.

What is claimed is:
1. A sales tracking system for managing the status of a sales cycle of intangible property, the system comprising:
  at least one processor;
  at least one input device;
  at least one display device; and
  at least one memory device which stores a plurality of instructions, which, when executed by the at least one processor, cause the at least one processor to operate with the at least one input device and the at least one display device to:
    (a) store a plurality of states of the sales cycle, the states including at least a contact state, an agree to purchase state, an application complete state, a medical information received state, and a client state;

(b) enable a user to input data about a potential customer;

(c) if the user inputs data about the potential customer, store an indication that the potential customer is associated with the contact state;

(d) if the potential customer agrees to purchase the intangible property, store an indication that the potential customer is associated with the agree to purchase state;

(e) if the potential customer provides a completed application, store an indication that the potential customer is associated with the application complete state;

(f) receive data indicative of medical information collected about the potential customer;

(g) if the data indicative of the medical information collected about the potential customer is received, store an indication that the potential customer is associated with the medical information received state; and (h) determine whether the potential customer has been associated with each of the contact state, the agree to purchase state, the application complete state, and the medical information received state, wherein:

(i) upon determining that the potential customer has been associated with each of the contact state, the agree to purchase state, the application complete state, and the medical information received state, automatically store an indication that the potential customer is in the client state and display an indication to provide the potential customer with the intangible property, and (ii) upon determining that the potential customer has not been associated with each of the contact state, the agree to purchase state, the application complete state, and the medical information received state, repeat (a) to (h).

2. The sales tracking system of claim 1, wherein when executed by the at least one processor, the plurality of instructions cause the at least one processor to operate with the at least one memory device to store a subset complete indication in association with the potential customer if the potential customer has been associated with some but not all of the contact state, the agree to purchase state, the application complete state, and the medical information received state.

3. The sales tracking system of claim 1, wherein when executed by the at least one processor, the plurality of instructions cause the at least one processor to operate with the at least one memory device to store a subset complete information in association with the potential customer if the potential customer has completed some but not all actions required to be associated with at least one of the contact state, the agree to purchase state, the application complete state, and the medical information received state.

4. The sales tracking system of claim 3, wherein when executed by the at least one processor, the plurality of instructions cause the at least one processor to operate with the at least one input device and the at least one display device to trigger at least one action based on the stored subset complete indication.

5. The sales tracking system of claim 1, wherein when executed by the at least one processor, the plurality of instructions cause the at least one processor to operate with the at least one input device and the at least one display device to trigger at least one action based on at least one selected from the group consisting of: an amount of time spent in one of the plurality of states of the sales cycle and a change from a first one of the plurality of states of the sales cycle to a second one of the plurality of states of the sales cycle.

6. The sales tracking system of claim 5, wherein the action is directed to a first user and not a second user based on a role associated with the first user.

7. The sales tracking system of claim 5, wherein the action includes associated information based on the change from the first one of the plurality of sales states of the sales cycle to the second one of the plurality of states of the sales cycle.

8. The sales tracking system of claim 7, wherein the associated information includes at least one selected from the group consisting of: a source of a lead, an identification of the user, an intangible product the potential customer is most likely to purchase, and a process the potential customer is most likely to complete.

9. The sales tracking system of claim 5, wherein the action includes at least one selected from the group consisting of: automatically sending an email, displaying a message, instructing the user to make a telephone call, generating a document, and creating a task.

10. The sales tracking system of claim 1, which is implemented as a customizable rules engine.

11. The sales tracking system of claim 1, wherein when executed by the at least one processor, the plurality of instructions cause the at least one processor to operate with the at least one input device and the at least one display device to automatically generate at least one report based on at least one selected from the group consisting of: a presence in one of the plurality of states of the sale cycle, an amount of time spent in one of the plurality of states of the sale cycle, and a change from a first one of the plurality of states of the sale cycle to a second one of the plurality of states of the sale cycle.

* * * * *